(12) United States Patent
    Shiuey

(10) Patent No.: US 10,792,245 B2
(45) Date of Patent: Oct. 6, 2020

(54) ANTIMICROBIAL POLYMER FOR USE IN OPHTHALMIC IMPLANTS

(71) Applicant: Yichieh Shiuey, San Jose, CA (US)

(72) Inventor: Yichieh Shiuey, San Jose, CA (US)

(73) Assignee: Keramed, Inc., Irvine, CA (US)

( * ) Notice: Subject to any disclaimer, the term of this patent is extended or adjusted under 35 U.S.C. 154(b) by 0 days.

(21) Appl. No.: 16/387,465

(22) Filed: Apr. 17, 2019

(65) Prior Publication Data

US 2019/0240153 A1 Aug. 8, 2019

Related U.S. Application Data

(63) Continuation of application No. 15/260,251, filed on Sep. 8, 2016, now Pat. No. 10,307,369.

(51) Int. Cl.
| | | |
|---|---|---|
| *A61K 9/00* | (2006.01) | |
| *A61L 27/16* | (2006.01) | |
| *A61L 27/24* | (2006.01) | |
| *A61L 27/18* | (2006.01) | |
| *A61L 27/54* | (2006.01) | |
| *A61L 27/26* | (2006.01) | |
| *A61L 27/36* | (2006.01) | |
| *A61L 27/50* | (2006.01) | |
| *C08G 18/83* | (2006.01) | |
| *C08L 33/00* | (2006.01) | |

(52) U.S. Cl.
CPC ............ *A61K 9/0051* (2013.01); *A61L 27/16* (2013.01); *A61L 27/18* (2013.01); *A61L 27/24* (2013.01); *A61L 27/26* (2013.01); *A61L 27/3641* (2013.01); *A61L 27/3687* (2013.01); *A61L 27/50* (2013.01); *A61L 27/54* (2013.01); *C08G 18/83* (2013.01); *C08L 33/00* (2013.01); *A61L 2300/208* (2013.01); *A61L 2300/404* (2013.01); *A61L 2430/16* (2013.01)

(58) Field of Classification Search
CPC ............................ A61K 9/0051; A61L 27/54
See application file for complete search history.

*Primary Examiner* — Kyle A Purdy
(74) *Attorney, Agent, or Firm* — Goldberg Cohen LLP

(57) ABSTRACT

An antimicrobial polymer for use in an ophthalmic implant, includes at least one antimicrobial monomer; and at least one other monomer selected from an acrylic, silicone, vinyl and collagen monomer.

12 Claims, 1 Drawing Sheet

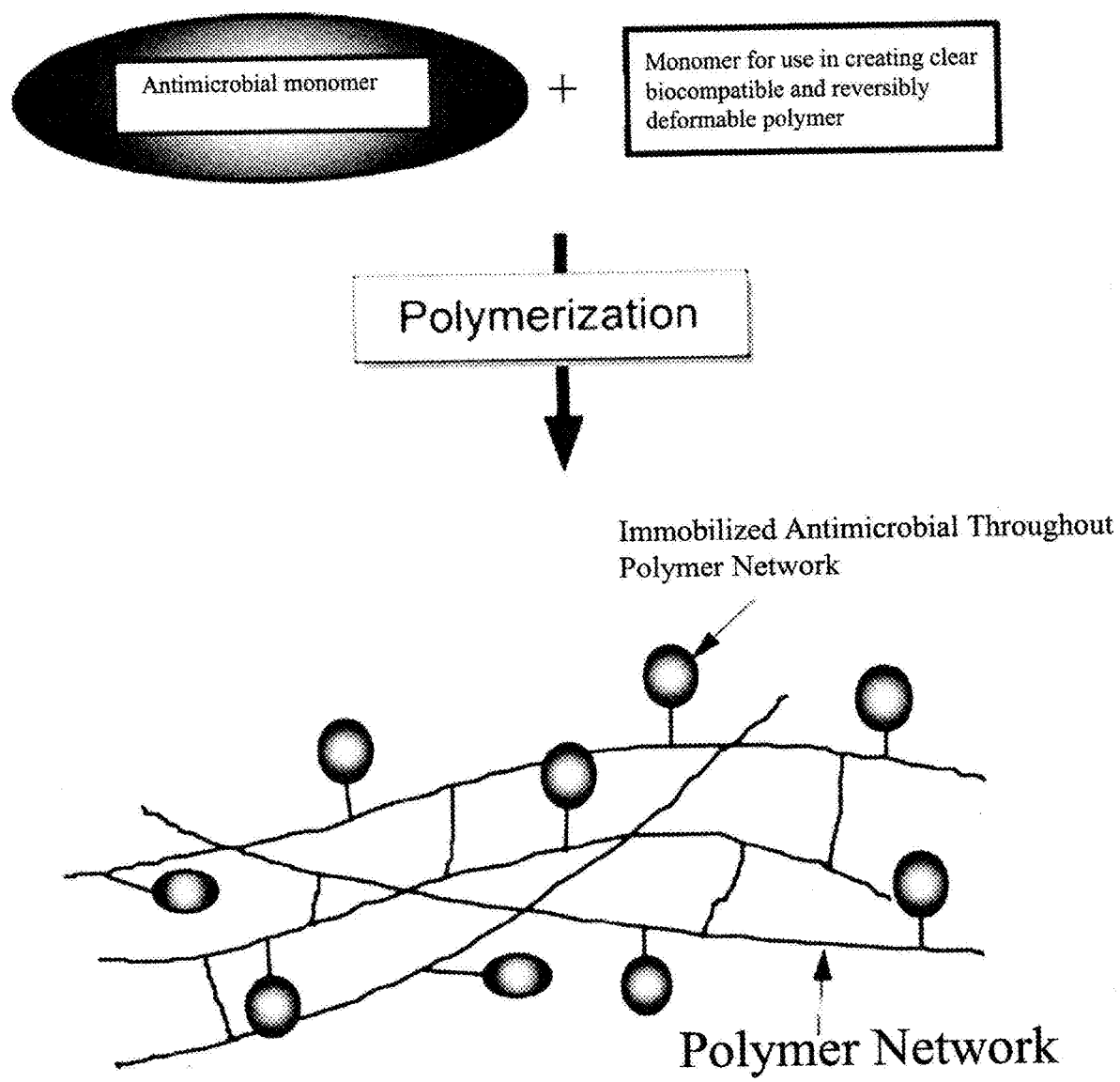

ANTIMICROBIAL POLYMER FOR USE IN OPHTHALMIC IMPLANTS

RELATED APPLICATIONS

The present application is a continuation of U.S. patent application Ser. No. 15/260,251 filed Sep. 8, 2016 (pending).

FIELD OF THE INVENTION

The present invention relates generally to ophthalmic implant devices and methods for their preparation and use, and more particularly, to antimicrobial polymers, obtained by copolymerizing at least one antimicrobial monomer with at least one other monomer for use in an ophthalmic implant device.

BACKGROUND OF THE INVENTION

Infections are serious complications of ophthalmic implant surgery. Examples of ocular implants include intraocular lenses, glaucoma valves, and artificial corneas, which are also known as keratoprostheses. An uncontrolled infection after ophthalmic implant surgery of any of these devices can result in loss of vision or even loss of the eye.

It is important to distinguish ophthalmic implants from contact lenses. Although both are considered medical devices, their purpose and requirements for proper functioning are very different.

Contact lenses are clear lenses that float on the human tear film. They are not physically attached to the eye in any way and direct contact between the contact lens and tissue is known to cause complications including corneal abrasions, infections and corneal scarring. A contact lens' purpose is to refract light to allow proper focus of light rays onto the retina.

By contrast, an ophthalmic implant is any device; clear, translucent or opaque, that can be embedded inside ocular tissue. An ophthalmic implant must be biocompatible with the ocular tissues in order to function.

The most common strategy used in reducing the risk of infection after ophthalmic implant surgery is the use of topical antibiotic drops. However, this regimen has the significant disadvantage of needing to rely on the patient's compliance to insure that the medications are dosed properly. The infection issue is especially troublesome in the case of artificial cornea implants, which currently require the daily administration of topical antibiotics drops for the life of the patient. The use of such antibiotics is necessary because current artificial corneas are exposed to the non-sterile surface of the eye. As such, there is a continual risk of infection.

Other inventors have recognized the inadequacy of antibiotic medications as a method of reducing infection after ophthalmic implant surgery. One alternative strategy that has been proposed is to either coat or covalently bond antibacterial chemicals to the surface of the ophthalmic implant as disclosed in U.S. Pat. No. 6,976,997 issued to Noolandi et al. A limitation of this method is that coatings and covalently bonded chemicals can be eroded away from the surface of the implant over time. Therefore, it is predictable that the antibacterial properties of these types of implants will decrease over time thereby increasing the risk of infection.

Another strategy, which has been proposed in the past, is to infuse the polymer of the ophthalmic implant with an antibacterial metal ion. In particular, silver and copper metal have been proposed as agents to be infused into polymers for use in an ophthalmic implant. Although, the use of free metal ions as an antibacterial agent within polymers has been used widely in commercial plastic goods and in some short-term disposable medical devices such as catheters, metal ions are known to be dangerous in the eye.

Argyrosis is the medical term for silver toxicity of the eye. Argyrosis has been reported to result in a slate gray discoloration of the conjunctiva and iris. Argyrosis has also been found to result in cataracts and retinal maculopathy, both of which are vision threatening conditions.

Copper toxicity in the eye results in a characteristic green ring around the cornea, which is termed a Kayser-Fleischer ring. Moreover, studies have demonstrated that copper toxicity can induce ocular complications such as intraocular inflammation (uveitis), hemorrhage, vitreous liquefaction, hypotony, iris ischemia and retinal damage.

In addition, free metal ions may also leach out of the polymer over time and therefore, the polymer may lose its antimicrobial properties over time.

For the stated reasons, there remains a need in the art for an improved composition and method of decreasing the risk of microbial infections after ophthalmic implant surgery.

SUMMARY OF THE INVENTION

The invention provides antimicrobial polymers for use in an ophthalmic implant obtained by copolymerizing at least one antimicrobial monomer and at least one monomer selected from an acrylic, silicone, vinyl or collagen monomer. The invention also provides methods for preparing an antimicrobial polymer for use in an ophthalmic implant, by reacting at least one antimicrobial monomer with at least one other monomer selected from an acrylic, silicone, vinyl and collagen monomer to provide the antimicrobial polymer; and using the antimicrobial polymer in the ophthalmic implant.

The copolymers of the present invention are antimicrobial, biocompatible, and reversibly deformable and are also clear, translucent or opaque. These characteristics are desirable for the optimal function of ophthalmic implants that are designed for implantation inside ocular tissue through small incisions. Moreover, because the entire co-polymer, not just the surface of the co-polymer, has antimicrobial properties, ophthalmic implants made from these types of co-polymers will not lose their antimicrobial properties even if the surface of the implant becomes eroded over time. This is particularly important for ophthalmic implants that are exposed to the surface of the eye, where blinking will cause erosion of the polymeric material. When the surface of the polymer of the present invention is eroded, the antimicrobial polymer beneath the surface will still kill microbes and thereby decrease the infection risk for the patient.

BRIEF DESCRIPTION OF THE DRAWINGS

FIG. 1 illustrates an embodiment of the polymerization of an antimicrobial, clear, biocompatible, reversibly deformable polymer.

DETAILED DESCRIPTION OF THE INVENTION

The present disclosure provides antimicrobial polymers for use in ophthalmic implants, which are obtained by copolymerizing at least one antimicrobial monomer with at least one other monomer selected from an acrylic, silicone, vinyl or collagen monomer. The resulting antimicrobial polymer provides an antimicrobial, biocompatible, and reversibly deformable implant, which are also clear, translucent or opaque. These characteristics are desirable for the optimal function of ophthalmic implants that are designed for implantation inside ocular tissues through small incisions. Moreover, because the entire copolymer, not just the surface of the copolymer, has antimicrobial properties, ophthalmic implants made from this type of copolymer will not lose their antimicrobial properties even if the surface of the implant becomes eroded over time. This is particularly important for ophthalmic implants which are exposed to the surface of the eye, where blinking will cause erosion of the polymeric material.

There are many types of ophthalmic implants. One type of such implant is an artificial cornea. In an artificial cornea the copolymer is contemplated to be antimicrobial, clear, biocompatible and reversibly deformable. In some cases, ophthalmic implants do not need to be clear to perform their intended function. For example, glaucoma valves, retinal prostheses and intracorneal implants outside of the visual axis do not need to refract light as part of their function and therefore, they may be translucent or opaque. In these cases the polymer of the present invention may be translucent or opaque. Various ophthalmic implants and methods thereof, have been fully described in U.S. Pat. Nos. 8,029,515; 7,901,421; and 7,223,275, each of which are hereby incorporated by reference in their entireties for all purposes.

Antimicrobial polymers are a class of polymers having antimicrobial activity, or the ability to inhibit the growth of microorganisms such as bacteria, fungi and/or protozoans. These polymers mimic antimicrobial peptides, which are used by the immune systems of living animals to kill various microbes. Antimicrobial polymers are generally nonvolatile and chemically stable, and are used in the areas of medicine as a means to fight infection, in the food industry to prevent bacterial contamination, and in water sanitation to inhibit the growth of microorganisms in drinking water.

Antimicrobial polymers kill microorganisms on contact by causing their cells to burst. For example, antimicrobial polymers generally possess a positive charge, and can be readily adsorbed onto the negative surface of the cell wall of a bacteria. Once adsorbed, the antimicrobial polymer then diffuses through the cell wall where it binds to and disrupts the cell membrane. While adsorption is best achieved by cationic antimicrobial polymers, small molecule antimicrobial agents excel at diffusion due to their low molecular weight. The disruption of the cell membrane and subsequent leakage of cytoplasmic constituents leads to the death of the bacteria.

Most bacterial cell walls are negatively charged and therefore, most antimicrobial polymers are positively charged to facilitate the adsorption process. The structure of the counter ion, or the ion associated with the polymer to balance charge, also affects the antimicrobial activity. Counter anions that form a strong ion-pair with the polymer impede the antimicrobial activity because the counter ion prevents the polymer from interacting with the bacteria. However, ions that form a loose ion-pair or readily dissociate from the polymer, exhibit a positive influence on the activity because it allows the polymer to interact freely with the bacteria.

FIG. 1 illustrates an embodiment of the polymerization of an antimicrobial, clear, biocompatible, reversibly deformable polymer. In this FIGURE, the antimicrobial polymers are obtained by copolymerizing at least one antimicrobial monomer with at least one monomer selected from an acrylic, silicone, vinyl or collagen monomer. After polymerization, the resulting polymeric network includes the immobilized antimicrobial polymer spaced throughout the network.

In an embodiment, the antibacterial monomer is selected from quaternary ammonium salt based monomers. A non-limiting example of a quaternary ammonium salt based monomer is 1-[12-(methacryloyloxy)dodecyl]pyridinium bromide (MDPB):

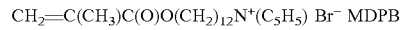

$CH_2=C(CH_3)C(O)O(CH_2)_{12}N^+(C_5H_5)\ Br^-$ MDPB

MDPB has been used as an antimicrobial monomer to reduce the risk of dental caries when copolymerized with dental adhesives and dental resins.

In other embodiments, the least one antimicrobial monomer is a quaternary ammonium salt based monomer such as methacryloxylethyl cetyl dimethyl ammonium chloride (DMAE-CB).

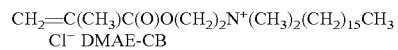

$CH_2=C(CH_3)C(O)O(CH_2)_2N^+(CH_3)_2(CH_2)_{15}CH_3$
$Cl^-$ DMAE-CB

It is also possible to increase the amount of antibacterial monomers that can be incorporated into polymeric materials and subsequently enhance the antibacterial activity by modifying the quaternary ammonium salt based monomers to have two polymerizable methacrylic moieties.

Thus, in other embodiments, the least one antimicrobial monomer is a quaternary ammonium salt based monomer such as 2-methacryloxyethyl dodecyl methyl ammonium bromide (MAE-DB):

$CH_2=C(CH_3)C(O)O(CH_2)_2N^+(CH_3)(CH_2)_2O(O)CC$
$(CH_3)=CH_2(CH_2)_{12}CH_3\ Br^-$ MAE-DB

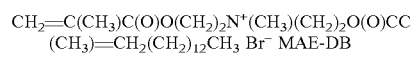

In other embodiments, the least one antimicrobial monomer is a quaternary ammonium salt based monomer such as 2-methacryloxyethyl hexadecyl methyl ammonium bromide (MAE-HB):

$CH_2=C(CH_3)C(O)O(CH_2)_2N^+(CH_3)(CH_2)_2O(O)CC$
$(CH_3)=CH_2(CH_2)_{16}CH_3\ Br^-$ MAE-HB

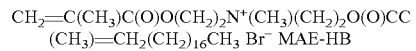

In other embodiments, the least one antimicrobial monomer is a quaternary ammonium salt based monomer such as bis(2-methacryloxyethyl) dimethyl ammonium bromide (IDMA-1):

$CH_2=C(CH_3)C(O)O(CH_2)_2N^+(CH_3)_2(CH_2)_2O(O)CC$
$(CH_3)=CH_2\ Br^-$ IDMA-1.

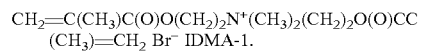

In other embodiments, the at least one antimicrobial monomer may differ based on the alkyl chain length. Examples of these include but are not limited to dimethylamino propyl methacrylate (DMAPM), dimethylamino hexyl methacrylate (DMAHM), dimethylamino heptyl methacrylate (DMAHPM), dimethylamino octyl methacrylate (DMAOM), dimethylamino nonyl methacrylate (DMANM), dimethylamino decyl methacrylate (DMADM), dimethylamino undecyl methacrylate (DMAUDM), dimethylamino dodecyl methacrylate (DMADDM), dimethylamino tridecyl methacrylate (DMATDM), dimethylamino tetradecyl methacrylate (DMATTDM), dimethylamino pentadecyl methacrylate (DMAPDM), dimethylamino hexadecyl methacrylate (DMAHDM), dimethylamino heptadecyl methacrylate (DMAHPDM), dimethylamino octadecyl methacrylate (DMAODM), dimethylamino nonadecyl methacrylate (DMANDM), dimethylamino icosyl methacrylate (DMAIOM), dimethylamino henicosyl methacrylate (DMAHOM), dimethylamino docosyl methacrylate (DMADOM), and/or combinations thereof.

In other embodiments, the antimicrobial monomer may have a primary, secondary or tertiary amino group.

Examples of these types of antibacterial monomers include but are not limited to ortho-, meta-, and/or para-dimethylaminomethyl styrene, N-[2-dimethylamino)ethyl]acrylamide, N-(2-aminoethyl)acrylamide, n-butylacrylamide, and diallyldimethyl ammonium salts.

In yet other embodiments, the antimicrobial monomer may be covalently linked to an antimicrobial peptide. Examples of antimicrobial peptides include but are not limited to: β-sheet peptides stabilized by two to four disulfide bridges (e.g., human α- and β-defensins, plectasin or protegrins); α-helical peptides (e.g., LL-37, cecropins or magainins); extended structures rich in glycine, proline, tryptophan, arginine or histidine (e.g., indolicidin); and loop peptides with one or disulfide bridge (e.g., bacteriocins).

In an embodiment, the at least one other monomer is selected from an acrylic, silicone, vinyl, or collagen monomer. These monomers can undergo polymerization with the at least one antimicrobial monomer described above to provide the antimicrobial polymers for use in ophthalmic implants. For example, the ophthalmic implant may be formed from a single blank or block of material typically a polysis hydrogel of a type commonly employed in for ring intraocular lenses (IOL's), such as a copolymer of hydroxyethyl methacrylate and methylmethacraylate, or a hydrophobic acrylic material. The polymeric hydrogel material could also have hydrophobic and hydrophilic properties, such as a copolymer of hydroxyethyl methacrylate and methylmethacraylate that has undergone plasma surface treatment. Alternatively, the ophthalmic in plant could be molded, machined, or laser cut from a collagen-based hydrogel.

In embodiments, the at least one other monomer is biocompatible with the cornea, the eye and the body. Suitable monomers include but are not limited to one or more monomers selected from collagen, urethanes, (2-hydroxyethylmethacrylate), vinylpyrolidone, glycerolmethacrylate, vinyl alcohol, ethylene glycol, methacrylic acid, silicones, acrylics, fluorocarbons, and monomers with phosphocholine.

In an embodiment, the at least one other monomer comprises a hydrogel. In other embodiments, the material comprises methacrylic acid and hydroxyethyl methacrylate (PHBMA/MAA).

In other embodiments, the at least one other monomer is a material comprising a reversibly deformable acrylic monomer, such as those used for intraocular lenses. Examples of suitable monomers include but are not limited to hydroxyethyl methacrylate and methyl methacrylate. In additional aspects, the monomers provide a deformable polymer that is hydrophilic in nature in order to allow smooth wetting of the optical surface of the implant. Wetability is an important characteristic of an ophthalmic implant to allow the tear film to act as a good optical interface.

In yet other embodiments, the ophthalmic implant may be manufactured from monomers that promote epithelialization on the surface of the implant. Examples of such materials include collagen and N-isopropylacryl amide, collagen and 1-ethyl-3.3'(dimethyl-aminopropyl)-carbodiimide as well as collagen and N-hydroxysuccinimide (EDC/NHS). In other aspects, the polymer may additionally contain extracellular matrix proteins such as fibronectin, laminin, substance P, insulin-like growth factor-1, or peptide sequences such as fibronectin adhesion-promoting or peptide (FAP).

In an embodiment, the at least one other monomer is an acrylic monomer. Non-limiting examples of an acrylic monomer include but are not limited to methyl acrylate (MA) and methyl methacrylate (MMA). MA and MMA are organic compounds having formula: $CH_2=CHCO_2CH_3$ and $CH_2=C(CH_3)CO_2CH_3$, respectively. These colorless liquids are produced on a large scale for the production of poly(methacrylate) (PMA) and poly(methyl methacrylate) (PMMA), respectively. While MA and MMA are irritants and possibly carcinogenic, polymers of MA and MMA are biocompatible, resistant to long exposure to temperatures, and the chemistry and cell action of human tissues. Acrylic monomers can undergo polymerization with the at least one antimicrobial monomer described above to provide the antimicrobial polymers for use in ophthalmic implants.

In an embodiment, the at least one other monomer is a silicone. Silicones have formula: $R_2SiO$, where R is an organic group such as methyl, ethyl, or phenyl. Silicones can undergo polymerization to form polysiloxanes, which include a repeating inorganic silicon-oxygen backbone chain (—Si—O—Si—O—Si—O—) with the organic side group R attached to the tetravalent silicon atom. By varying the —Si—O— chain lengths, side groups, and cross linking, polysiloxanes can be synthesized with a wide variety of properties and compositions. They can vary in consistency from liquid to gel to rubber to hard plastic. The most common siloxane is the linear polydimethylsiloxane (PDMS), a silicone oil. Silicone monomers can also undergo polymerization with the at least one antimicrobial monomer described above to provide the antimicrobial polymers for use in ophthalmic implants.

In an embodiment, the at least one other monomer is a vinyl monomer. Non-limiting examples of a vinyl monomer include but are not limited to vinyl esters (acrylates), vinyl carbonates (ROC(O)OCH=$CH_2$), and vinyl carbamates (R'R"NC(O)OCH=$CH_2$). These monomers have been shown to be generally suitable for many biomedical applications. In particular, monomers like vinyl carbonates and vinyl carbamates generally have lower cytotoxicity yet similar reactivity to acrylates. For example, degradation vinyl carbonates and vinyl carbamates can be easily tuned to provide non-toxic low molecular weight polyvinyl alcohol as degradation product and various other non-toxic alcohols such as glycerol or polyethylene glycol. This concept has also been used to provide vinyl ester derivatives of hyaluronic acid and gelatin in the field of hydrogels for tissue engineering. Vinyl monomers can also undergo polymerization with the at least one antimicrobial monomer described above to provide the antimicrobial polymers for use in ophthalmic implants.

In an embodiment, the at least one other monomer is a collagen monomer. A single collagen molecule, tropocollagen, is used to make up larger collagen aggregates, such as fibrils. Fibrils are made up of three polypeptide strands, each of which has the confirmation of a left-handed helix. These three left-handed helices are twisted together into a right-handed triple helix or microfibril, a cooperative quaternary structure stabilized by hydrogen bonds. Each microfibril is then interdigitated with its neighboring microfibrils. Moreover, collagen monomers may be linked to one or more acrylate or vinyl monomers using various linkers. Collagen monomers can also undergo polymerization with the at least one antimicrobial monomer described above to provide the antimicrobial polymers for use in ophthalmic implants. In an embodiment, the ophthalmic implant may include collagen and N-isopropylacrylamide, collagen and 1-ethyl-3,3'(dimethyl-aminopropyl)-carbodiimide as well as collagen and N-hydroxysuccinimide (EDC/NHS).

In the preceding description, the present disclosure is described with reference to specifically exemplary embodiments thereof. It will, however, be evident that various modifications and changes may be made thereto without departing from the broader spirit and scope of the present disclosure, as set forth in the claims. The specification and drawings are, accordingly, to be regarded as illustrative and not as restrictive. It is understood that the present disclosure is capable of using various other combinations and embodiments and is capable of any changes or modifications within the scope of the inventive concept as expressed herein.

What is claimed is:

1. An ophthalmic implant comprising an antimicrobial polymer, comprising:
   at least one antimicrobial monomer, wherein the antimicrobial monomer is a quaternary ammonium salt based monomer selected from 1-[12-(methacryloyloxy)dodecyl]-pyridinium bromide (MDPB), methacryloxylethyl cetyl dimethyl ammonium chloride (DMAE-CB), 2-methacryloxyethyl dodecyl methyl ammonium bromide (MAE-DB), 2-methacryloxyethyl hexadecyl methyl ammonium bromide (MAE-HB), and bis(2-methacryloxyethyl) dimethyl ammonium bromide (IDMA-1); and,
   at least one other monomer selected from an acrylic, vinyl and collagen monomer; and,
   wherein the ophthalmic implant is an intraocular lens.

2. The ophthalmic implant according to claim 1, wherein the antimicrobial polymer is clear, opaque, or translucent.

3. The ophthalmic implant according to claim 1, wherein the antimicrobial polymer is reversibly deformable.

4. The ophthalmic implant according to claim 1, wherein the at least one other monomer is an acrylic monomer selected from methyl acrylate (MA) and methyl methacrylate (MMA), or a vinyl monomer selected from a vinyl carbonate and a vinyl carbamate.

5. An ophthalmic implant comprising an antimicrobial polymer, comprising:
   at least one antimicrobial monomer, wherein the antimicrobial monomer is a quaternary ammonium salt based monomer selected from 1-[12-(methacryloyloxy)dodecyl]-pyridinium bromide (MDPB), methacryloxylethyl cetyl dimethyl ammonium chloride (DMAE-CB), 2-methacryloxyethyl dodecyl methyl ammonium bromide (MAE-DB), 2-methacryloxyethyl hexadecyl methyl ammonium bromide (MAE-HB), and bis(2-methacryloxyethyl) dimethyl ammonium bromide (IDMA-1); and,
   at least one other monomer selected from an acrylic, vinyl and collagen monomer, wherein the antimicrobial polymer is for use in an ophthalmic implant; and,
   wherein the ophthalmic implant is an intraocular lens.

6. The ophthalmic implant according to claim 5, wherein the at least one other monomer is an acrylic monomer selected from methyl acrylate (MA) and methyl methacrylate (MMA), or a vinyl monomer selected from a vinyl carbonate and a vinyl carbamate.

7. The ophthalmic implant according to claim 5, wherein the antimicrobial polymer is clear, opaque, or translucent.

8. The ophthalmic implant according to claim 5, wherein the antimicrobial polymer is reversibly deformable.

9. An ophthalmic implant comprising an antimicrobial polymer, comprising:
   at least one antimicrobial monomer, wherein the antimicrobial monomer is a quaternary ammonium salt based monomer selected from 1-[12-(methacryloyloxy)dodecyl]-pyridinium bromide (MDPB), methacryloxylethyl cetyl dimethyl ammonium chloride (DMAE-CB), 2-methacryloxyethyl dodecyl methyl ammonium bromide (MAE-DB), 2-methacryloxyethyl hexadecyl methyl ammonium bromide (MAE-HB), and bis(2-methacryloxyethyl) dimethyl ammonium bromide (IDMA-1); and,
   and at least one other monomer selected from an acrylic, vinyl and collagen monomer, wherein the antimicrobial polymer is formed into an ophthalmic implant; and,
   wherein the ophthalmic implant is an intraocular lens.

10. The ophthalmic implant according to claim 9, wherein the at least one other monomer is an acrylic monomer selected from methyl acrylate (MA) and methyl methacrylate (MMA) or a vinyl monomer selected from a vinyl carbonate and a vinyl carbamate.

11. The ophthalmic implant according to claim 9, wherein the antimicrobial polymer is clear, opaque, or translucent.

12. The ophthalmic implant according to claim 9, wherein the antimicrobial polymer is reversibly deformable.

* * * * *